United States Patent
Wada et al.

(10) Patent No.: US 11,406,395 B2
(45) Date of Patent: *Aug. 9, 2022

(54) HEMOSTATIC DEVICE

(71) Applicant: TERUMO KABUSHIKI KAISHA, Tokyo (JP)

(72) Inventors: Satoshi Wada, Fujinomiya (JP); Shigeki Numata, Fujinomiya (JP); Hiroshi Yagi, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 361 days.

This patent is subject to a terminal disclaimer.

(21) Appl. No.: 16/793,541

(22) Filed: Feb. 18, 2020

(65) Prior Publication Data

US 2020/0178983 A1    Jun. 11, 2020

Related U.S. Application Data

(60) Continuation of application No. 15/705,483, filed on Sep. 15, 2017, now Pat. No. 10,610,238, which is a
(Continued)

(30) Foreign Application Priority Data

Jul. 15, 2002 (JP) .................................. 2002-206295
Nov. 7, 2002 (JP) .................................. 2002-323940
Dec. 24, 2002 (JP) .................................. 2002-373013

(51) Int. Cl.
*A61F 5/28* (2006.01)
*A61F 13/00* (2006.01)
(Continued)

(52) U.S. Cl.
CPC ........ *A61B 17/135* (2013.01); *A61B 17/1325* (2013.01); *A61B 2017/00907* (2013.01);
(Continued)

(58) Field of Classification Search
CPC .... A61F 5/34; A61F 5/30; A61F 5/32; A61M 39/00; A61B 5/022; A61B 17/135;
(Continued)

(56) References Cited

U.S. PATENT DOCUMENTS 37,156 A    12/1862  Dunton et al.
3,905,361 A  9/1975  Hewson et al.
(Continued)

FOREIGN PATENT DOCUMENTS

EP    0601756 A1    6/1994
EP    1382306 A2    1/2004
(Continued)

OTHER PUBLICATIONS

Advisory Action dated Dec. 12, 2007, for U.S. Appl. No. 10/618,964, filed Jul. 15, 2003, three pages.
(Continued)

*Primary Examiner* — Tarla R Patel
(74) *Attorney, Agent, or Firm* — Buchanan Ingersoll & Rooney PC

(57) ABSTRACT

A hemostatic device includes a flexible band adapted to be wrapped around a patient's limb at a site on the limb where bleeding is to be stopped, a portion for securing the band in a wrapped state to the limb, a curved plate which is made of a material more rigid than the band and at least a portion of which is curved toward the inner peripheral side thereof, a main balloon which is provided on the inner peripheral side of the curved plate and which inflates when a fluid is introduced therein, and a pressing member which is provided between the curved plate and the main balloon so that at least a portion thereof overlaps with the balloon and which is adapted for pressing against the balloon. The device
(Continued)

provides an excellent hemostatic effect and prevents numbness and poor circulation in areas peripheral to the site of attachment.

20 Claims, 7 Drawing Sheets

Related U.S. Application Data continuation of application No. 15/229,455, filed on Aug. 5, 2016, now Pat. No. 10,219,809, which is a continuation of application No. 13/889,112, filed on May 7, 2013, now abandoned, which is a continuation of application No. 12/356,969, filed on Jan. 21, 2009, now Pat. No. 8,481,803, which is a division of application No. 10/618,964, filed on Jul. 15, 2003, now Pat. No. 7,498,477.

(51) Int. Cl.
*A61L 15/00* (2006.01)
*A61B 17/00* (2006.01)
*A61B 17/135* (2006.01)
*A61B 17/132* (2006.01)
*A61B 17/12* (2006.01)
*A61B 90/00* (2016.01)

(52) U.S. Cl.
CPC .............. *A61B 2017/12004* (2013.01); *A61B 2090/3937* (2016.02)

(58) Field of Classification Search
CPC ...... A61B 17/1325; A61B 2017/00907; A61B 2017/12004; A61B 2090/3937
USPC ....... 128/99.1, 100.1, 118.1; 602/13, 53, 75, 602/76; 606/201–203
See application file for complete search history.

(56) References Cited

U.S. PATENT DOCUMENTS

| | | | |
|---|---|---|---|
| 4,469,099 A | 9/1984 | Mcewen | |
| 4,920,971 A | 5/1990 | Blessinger | |
| 4,981,133 A | 1/1991 | Rollband | |
| 5,152,302 A | 10/1992 | Fareed | |
| 5,269,803 A | 12/1993 | Geary et al. | |
| 5,295,951 A | 3/1994 | Fareed | |
| 5,307,811 A | 5/1994 | Sigwart et al. | |
| 5,433,724 A | 7/1995 | Kawasaki et al. | |
| 5,464,420 A | 11/1995 | Hori et al. | |
| 5,496,262 A | 3/1996 | Johnson, Jr. et al. | |
| 5,514,155 A | 5/1996 | Daneshvar | |
| 5,569,297 A | 10/1996 | Makower et al. | |
| 5,643,315 A | 7/1997 | Daneshvar | |
| 5,660,182 A | 8/1997 | Kuroshaki et al. | |
| 5,779,657 A | 7/1998 | Daneshvar | |
| 5,792,173 A | 8/1998 | Breen et al. | |
| 5,840,037 A | 11/1998 | Tochikubo et al. | |
| 6,007,562 A | 12/1999 | Harren et al. | |
| 6,336,901 B1 | 1/2002 | Itonaga et al. | |
| 6,361,496 B1 | 3/2002 | Zikorus et al. | |
| 6,527,727 B2 | 3/2003 | Itonaga et al. | |
| 6,694,821 B2 | 2/2004 | Yamakoshi et al. | |
| 6,827,727 B2 | 12/2004 | Stålemark et al. | |
| 7,498,477 B2 * | 3/2009 | Wada ................ | A61B 17/1325 602/76 |
| 7,927,295 B2 | 4/2011 | Bates et al. | |
| 8,034,009 B2 | 10/2011 | Bates et al. | |
| 8,481,803 B2 * | 7/2013 | Wada ................ | A61B 17/135 602/76 |
| 8,481,805 B2 | 7/2013 | Wada et al. | |
| 8,524,974 B2 * | 9/2013 | Wada ................ | A61B 17/1325 602/76 |
| 8,759,603 B2 * | 6/2014 | Wada ................ | A61B 17/135 602/53 |
| 9,895,155 B2 | 2/2018 | Wada et al. | |
| 9,936,959 B2 * | 4/2018 | Wada ................ | A61B 17/135 |
| 9,949,741 B2 * | 4/2018 | Wada ................ | A61B 17/135 |
| 10,058,334 B1 | 8/2018 | Wada et al. | |
| 10,219,809 B2 * | 3/2019 | Wada ................ | A61B 17/1325 |
| 10,610,238 B2 * | 4/2020 | Wada ................ | A61B 17/135 |
| 2002/0170359 A1 | 11/2002 | Yamakoshi et al. | |
| 2003/0199922 A1 | 10/2003 | Buckman | |
| 2004/0049214 A1 | 3/2004 | Akerfeldt | |
| 2004/0122469 A1 | 6/2004 | Akerfeldt et al. | |
| 2013/0245674 A1 | 9/2013 | Wada et al. | |
| 2013/0282048 A1 | 10/2013 | Wada et al. | |
| 2013/0289613 A1 | 10/2013 | Wada et al. | |
| 2016/0338709 A1 | 11/2016 | Wada et al. | |
| 2018/0000491 A1 | 1/2018 | Wada et al. | |
| 2018/0000492 A1 | 1/2018 | Wada et al. | |
| 2018/0000493 A1 | 1/2018 | Wada et al. | |
| 2018/0000494 A1 | 1/2018 | Wada et al. | |
| 2018/0014833 A1 | 1/2018 | Wada et al. | |
| 2018/0077761 A1 | 3/2018 | Takahashi et al. | |

FOREIGN PATENT DOCUMENTS

| | | | |
|---|---|---|---|
| EP | 2070483 A2 | 6/2009 | |
| EP | 2245998 A1 | 11/2010 | |
| JP | 5633526 Y2 | 8/1981 | |
| JP | 05305093 A | 11/1993 | |
| JP | 0779983 A | 3/1995 | |
| JP | 0871077 A | 3/1996 | |
| JP | 08140990 A | 6/1996 | |
| JP | 3031486 U | 11/1996 | |
| JP | 1057386 A | 3/1998 | |
| JP | 2000515773 A | 11/2000 | |
| WO | 9702783 A1 | 1/1997 | |
| WO | 9717900 A1 | 5/1997 | |
| WO | 2012126154 A1 | 9/2012 | |

OTHER PUBLICATIONS

Advisory Action dated Aug. 17, 2012, for U.S. Appl. No. 12/356,969, filed Jan. 21, 2009, three pages.
Advisory Action dated Jul. 1, 2011, for U.S. Appl. No. 12/356,969, filed Jan. 21, 2009, three pages.
Partial European Search Report mailed on May 13, 2009, for European Patent Application No. 09 156 834.5, filed on Jul. 15, 2003, four pages.
Extended European Search Report dated Jul. 10, 2009, for European Patent Application No. 09 156 834.5, filed on Jul. 15, 2003, ten pages.
European Communication dated Jan. 8, 2010, for European Patent Application No. 09 156 834.5, filed on Jul. 15, 2003, one page.
Extended European Search Report dated Aug. 6, 2010, for European Patent Application No. 10 167 429.9, filed on Jul. 15, 2003, five pages.
Partial European Search Report dated Feb. 9, 2004, for European Patent Application No. 03 016 024.6, filed on Jul. 15, 2003, five pages.
Extended European Search Report dated May 6, 2004, for European Patent Application No. 03 016 024.6, filed on Jul. 15, 2003, five pages.
Final Office action dated Mar. 29, 2012, for U.S. Appl. No. 12/356,969, filed Jan. 21, 2009, eight pages.
Final Office action dated Aug. 21, 2007, for U.S. Appl. No. 10/618,964, filed Jul. 15, 2003, eight pages.
Final Office action dated Dec. 5, 2013, for U.S. Appl. No. 13/922,052, filed Jun. 19, 2013, fifteen pages.
Non-Final Office action dated Aug. 17, 2011, for U.S. Appl. No. 12/356,969, filed Jan. 21, 2009, nine pages.
Non-Final Office action dated Nov. 29, 201 0, for U.S. Appl. No. 12/356,969, filed Jan. 21, 2009, seven pages.
Non-Final Office action dated Oct. 16, 2012, for U.S. Appl. No. 12/356,969, filed Jan. 21, 2009, eight pages.

(56) References Cited

OTHER PUBLICATIONS

Non-Final Office action dated Mar. 13, 2007, for U.S. Appl. No. 10/618,964, filed Jul. 15, 2003, seven pages.
Non-Final Office action dated Mar. 11, 2008, for U.S. Appl. No. 10/618,964, filed Jul. 15, 2003, seven pages.
Non-Final Office action dated May 10, 2013, for U.S. Appl. No. 13/725,269, filed Dec. 21, 2012, nine pages.
Non-Final Office action dated Aug. 16, 2013, for U.S. Appl. No. 13/922,052, filed Jun. 19, 2013, thirteen pages.
Non-Final Office action dated Mar. 29, 2013, for U.S. Appl. No. 13/725,406, filed Dec. 21, 2012, nine pages.
Notice of Allowance dated May 1, 2013, for U.S. Appl. No. 13/725,406, filed Dec. 21, 2012, ten pages.
Notice of Allowance dated Jul. 24, 2013, for U.S. Appl. No. 13/725,269, filed Dec. 21, 2012, ten pages.
Notice of Allowance dated Oct. 20, 2008, for U.S. Appl. No. 10/618,964, filed Jul. 15, 2003, eight pages.
Notice of Allowance dated May 24, 2013, for U.S. Appl. No. 12/356,969, filed Jan. 21, 2009, nine pages.
Notice of Allowance dated Feb. 6, 2009, for European Patent Application No. 03 016 024.6, filed on Jul. 15, 2003, seven pages.
Notice of Allowance dated Sep. 9, 201 o, for European Patent Application No. 09 156 834.5, filed on Jul. 15, 2003, seven pages.
Notice of Allowance dated Jul. 18, 2011, for European Patent Application No. 10 167 429.9, filed on Jul. 15, 2003, seven pages.
European Communication dated May 11, 2006, for European Patent Application No. 03 016 024.6, filed on Jul. 15, 2003, five pages.
European Communication dated May 21, 2007, for European Patent Application No. 03 016 024.6, filed on Jul. 15, 2003, three pages.
Japanese Office Action dated Oct. 11, 2007 for Japanese Patent Application No. 2006-346282 (with full English Translation).
Japanese Office Action dated Feb. 5, 2008 for Japanese Patent Application No. 2002-373013 (with full English Translation).
Japanese Office Action dated Apr. 27, 2010 for Japanese Patent Application No. 2008-29849 (with Partial English Translation).
Partial European Search Report dated May 13, 2009, for European Patent Application No. 09 156 834.5, filed on Jul. 15, 2003, four pages.

* cited by examiner

HEMOSTATIC DEVICE

CROSS-REFERENCES TO RELATED APPLICATIONS

This application is a continuation of U.S. application Ser. No. 15/705,483 filed on Sep. 15, 2017, which is a continuation of U.S. application Ser. No. 15/229,455 filed on Aug. 5, 2016, now U.S. Pat. No. 10,219,809, which is a continuation of U.S. application Ser. No. 13/889,112 filed on May 7, 2013, now abandoned, which is a continuation of U.S. application Ser. No. 12/356,969 filed on Jan. 21, 2009, now U.S. Pat. No. 8,481,803, which is a divisional application of U.S. application Ser. No. 10/618,964 filed on Jul. 15, 2003, now U.S. Pat. No. 7,498,477, and claims priority to Japanese Application No. 2002-206295 filed on Jul. 15, 2002, Japanese Application No. 2002-323940 filed on Nov. 7, 2002 and Japanese Application No. 2002-373013 filed on Dec. 24, 2002 the entire content of all of which is incorporated herein by reference.

FIELD OF THE INVENTION

The present invention relates to a hemostatic device, and more particularly to a hemostatic device which is attached to a patient's limb at a site on the limb where bleeding is to be stopped and which, by the inflation of a balloon, applies pressure to the site so as to stop bleeding.

BACKGROUND DISCUSSION

When a procedure involving the percutaneous insertion of an instrument such as a catheter into a blood vessel is carried out for medical treatment, examination or diagnosis, bleeding at the puncture site must be stopped following subsequent withdrawal and removal of the catheter. Hemostatic devices which are attached by being wrapped around the portion of an arm or leg where the puncture site is located and compress the puncture site where bleeding is to be stopped are already known in the prior art (e.g., JP 3031486 U).

In such prior-art hemostatic devices, the pressure applied to the site where bleeding is to be stopped is directed in a substantially vertically downward direction, and the hemostatic effect in this pressing direction is inadequate. Therefore, complete hemostasis sometimes does not occur or takes a long time to achieve.

Moreover, prior-art hemostatic devices apply pressure not only to the puncture site where bleeding is to be stopped, but to the surrounding area as well. Hence, other tissues are also compressed, including other blood vessels and nerves, sometimes resulting in numbness and poor blood circulation.

To keep this from happening, a health care practitioner such as a physician or nurse must lower the compressive force over time by carrying out manual operations to reduce the balloon pressure or loosen the band, which is inefficient and inconvenient.

In addition, when using such prior-art hemostatic devices, the health care practitioner visually sights the balloon into place over the puncture site. It has been pointed out that this makes the balloon difficult to position properly. In fact, due to poor positioning of the balloon, a hematoma may form or blood leakage may occur because of the inability to stop bleeding.

SUMMARY

The hemostatic device disclosed here has an excellent hemostatic effect.

The hemostatic device disclosed here also spontaneously (that is, without manipulation by a health care practitioner such as a physician or nurse-sometimes referred to hereinafter as the "operator") eases over time the pressure applied by the balloon, thus helping to prevent harmful effects from the continued application of pressure, such as numbness, pain and vascular blockage.

The disclosed hemostatic device enables a balloon for compressing a puncture site (a site where blood flow is to be stopped) to be easily positioned at the site, and thus minimizes blood leakage and hematoma formation due to poor positioning of the balloon.

One aspect of the disclosure involves a hemostatic device to stop bleeding at a puncture site on a limb of a patient, wherein the hemostatic device comprises: a flexible band portion and a more rigid portion, with the flexible band portion being configured to be wrapped around at least a portion of the limb of the patient to apply the hemostatic device to the limb of the patient, and the more rigid portion and the flexible band portion possessing an inner side that faces toward the limb of the patient when the hemostatic device is applied to the patient's limb. An inflatable balloon which inflates when a fluid is introduced into the balloon is positioned to contact a surface of the patient's limb when the balloon is inflated while the hemostatic device is applied to the limb of the patient. The inner side of the more rigid portion comprises a curved inner side part that is curved, and a marker is positioned in alignment with the center of the balloon to facilitate positioning the hemostatic device when applying the hemostatic device to the limb of the patient so that when the hemostatic device is applied to the limb of the patient the marker overlies the puncture site. The inflatable balloon is located at the inner side of the more rigid portion so that the inflatable balloon is between the inner side of the more rigid portion and the limb of the patient when the hemostatic device is applied to the limb of the patient. The balloon is positioned relative to the curved inner side part of the more rigid portion such that when the hemostatic device is applied to the limb of the patient and the inflatable balloon is inflated, a part of the curved inner side of the more rigid part overlies the balloon and the balloon applies a compression force to a puncture site in an oblique direction with respect to a surface of the limb. The curved inner side part of the more rigid portion overlaps the marker as seen in a plan view from the inner side of the more rigid portion and the flexible band portion.

According to another aspect, a hemostatic device to stop bleeding at a puncture site on a limb of a patient comprises a flexible band configured to be wrapped around at least a portion of a limb of a patient to apply the hemostatic device to the limb of the patient, wherein the flexible band possesses opposite end portions, with at least one of the end portions overlapping another portion of the flexible band when the hemostatic device is applied to the limb of the patient. A plate is held on the flexible band at a position between the two end portions of the flexible band, with the plate being more rigid than the flexible band and the plate possessing an inner side that faces toward the limb of the patient when the hemostatic device is applied to the limb of the patient. An inflatable balloon inflates when a fluid is introduced into the balloon and is positioned to contact a surface of the patient's limb when the balloon is inflated while the hemostatic device is applied to the limb of the patient. The inner side of the plate includes a curved inner side part that is curved and a flat inner side part that is flat. A visually viewable marker facilitates positioning the hemostatic device on the limb of the patient so that the balloon is positioned to apply a compression force to a puncture site in an oblique direction with respect to a surface of the limb. The inflatable balloon is located at the inner side of the plate so that the inflatable balloon is between the inner side of the plate and the limb of the patient when the hemostatic device is applied to the limb of the patient. The balloon is positioned relative to the curved inner side part of the plate such that when the hemostatic device is applied to the limb of the patient and the inflatable balloon is inflated, a part of the curved inner side of the plate overlies the balloon and the balloon applies a compression force to a puncture site in the oblique direction with respect to the surface of the limb. The curved inner side part of the plate overlaps the marker as seen in a plan view from the inner side of the plate and the flexible band.

A further aspect of the disclosure here involves a hemostatic device to stop bleeding at a puncture site on a limb of a patient. The hemostatic device comprises a flexible band configured to be wrapped around at least a portion of a limb of a patient to apply the hemostatic device to the limb of the patient, and a plate on the flexible band. The flexible band possesses opposite end portions spaced apart from one another in a lengthwise direction of the flexible band, with at least one of the end portions overlapping another portion of the flexible band when the hemostatic device is applied to the limb of the patient. The plate is more rigid than the flexible band and possesses an inner side that faces toward the limb of the patient when the hemostatic device is applied to the limb of the patient. An inflatable balloon inflates when a fluid is introduced into the balloon, wherein the balloon is positioned to contact a surface of the patient's limb when the balloon is inflated while the hemostatic device is applied to the limb of the patient. The inner side of the plate includes a curved inner side part, and the balloon is located at the inner side of the plate so that the balloon is between the inner side of the plate and the limb of the patient when the hemostatic device is applied to the limb of the patient. The balloon being is located on the inner side of the plate at a position deviated to a first end of the plate from a center of the plate in the lengthwise direction of the flexible band. A marker is positioned in alignment with a center of the balloon to facilitate positioning the hemostatic device when applying the hemostatic device to the limb of the patient so that when the hemostatic device is applied to the limb of the patient the marker overlies the puncture site. The balloon is positioned relative to the curved inner side part of the plate such that when the hemostatic device is applied to the limb of the patient and the inflatable balloon is inflated, a part of the curved inner side of the plate overlies the balloon and the balloon applies a compression force to a puncture site in an oblique direction with respect to a surface of the limb. The curved inner side part of the plate overlaps the marker as seen in a plan view from the inner side of the plate.

These and other aspects, features and advantages of the hemostatic device and method disclosed here will become more apparent upon consideration of the following detailed description and the accompanying drawings.

DETAILED DESCRIPTION OF THE INVENTION

First Embodiment

As noted above, FIG. 1 is a bottom view of a first embodiment of the hemostatic device according to the invention. This shows the side of the device that serves as the inside surface when the device is attached to the wrist of a patient. FIG. 2 is a sectional view showing the same hemostatic device attached and in use on the wrist.

Figure 1:
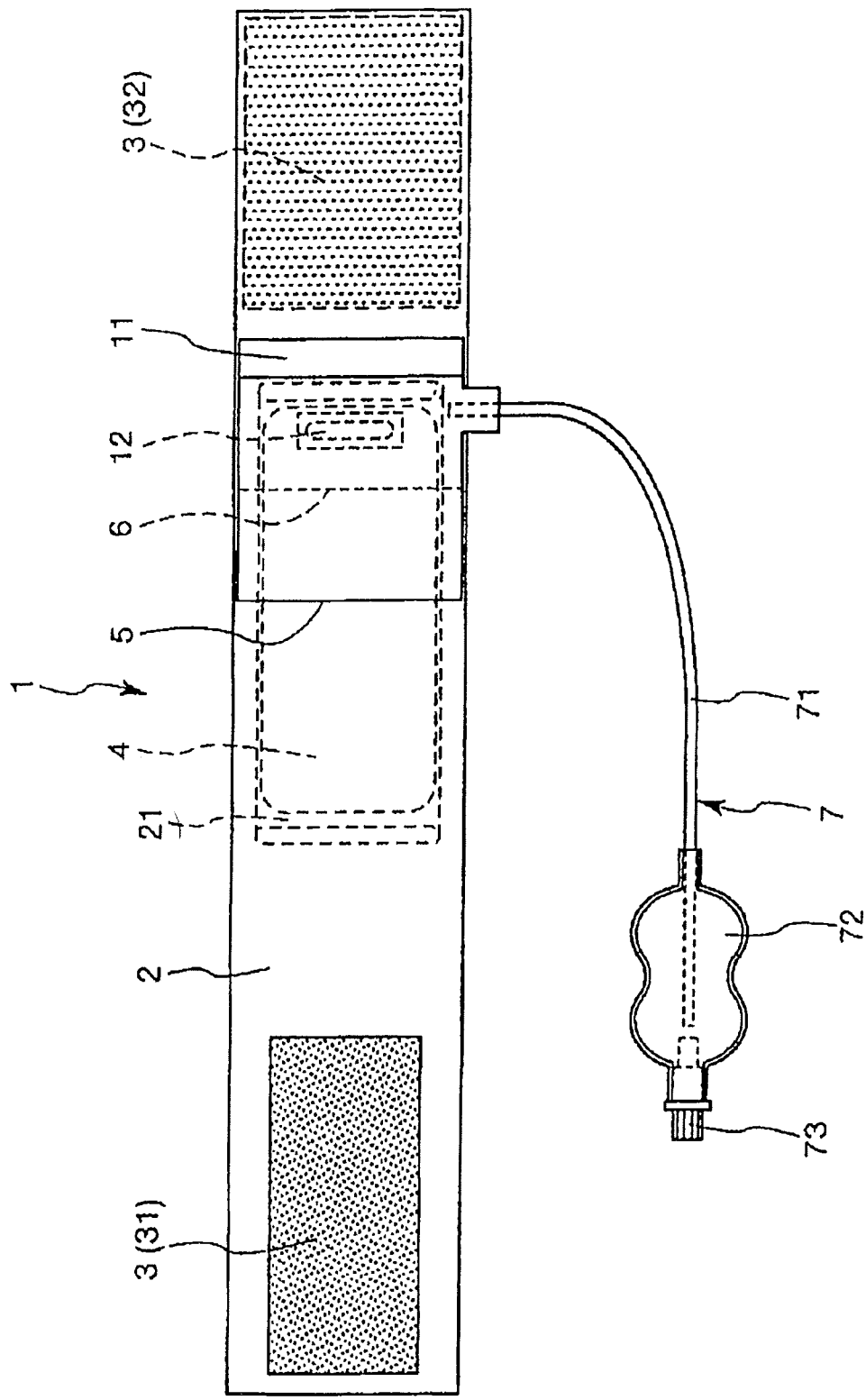
FIG. 1 is a bottom view of a first embodiment of the hemostatic device according to the invention. This shows the side of the device that serves as the inside surface when the device is attached to the wrist of a patient.
Figure 2:
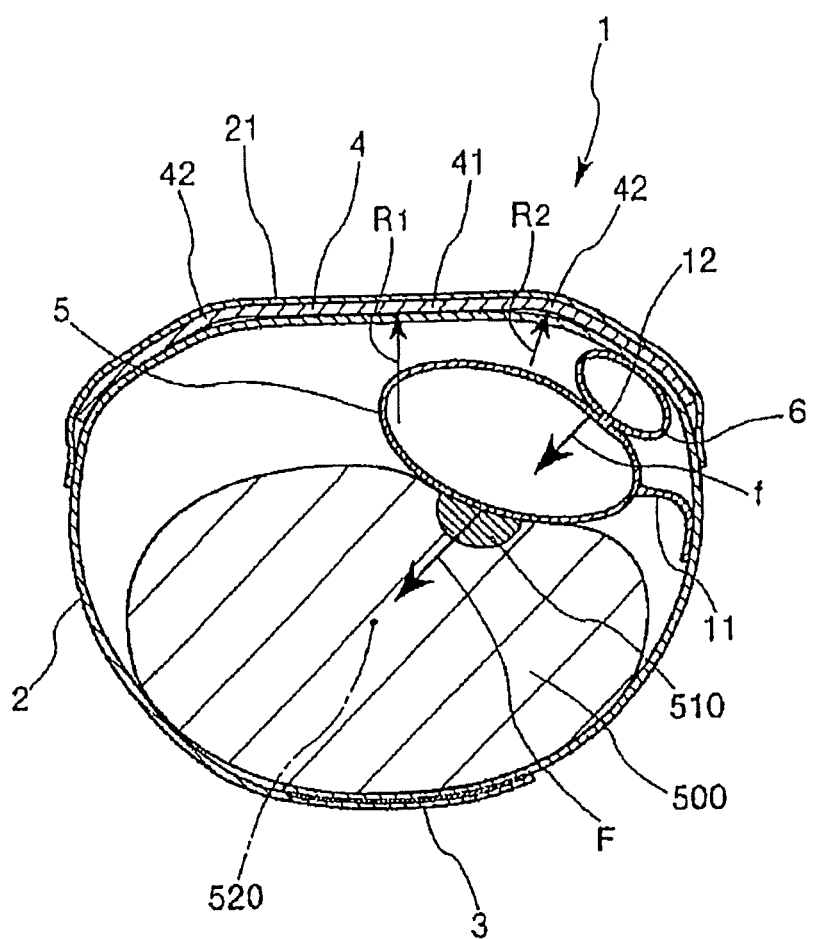
FIG. 2 is a sectional view showing the same hemostatic device as in FIG. 1 during use.

The hemostatic device 1 shown in FIGS. 1 and 2 is used to stop bleeding at a puncture site 510 following the removal of an instrument such as a catheter which was inserted percutaneously into an artery through a puncture formed somewhere on a limb, such as at a wrist 500, for a medical purpose such as treatment, examination or diagnosis. This hemostatic device 1 has a band 2 which is adapted to be wrapped around the wrist 500, a surface fastener 3 for securing the band 2 in a wrapped state to the wrist 500, a curved plate 4, a main balloon 5 and a secondary balloon 6.

The band 2 is a flexible belt-like member. As shown in FIG. 2, the band 2 is attached to the wrist 500 by being wrapped one full turn around the outside of the wrist 500 and having portions of the band 2 near both ends thereof mutually overlap. The overlapping portions of the band 2 are then secured, or joined, by means of the subsequently described surface fastener 3.

The material making up the band 2 is not subject to any particular limitation, as far as the puncture site 510 can be seen therethrough. Illustrative examples include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicones, polyurethanes various thermoplastic elastomers such as polyamide elastomers, polyurethane elastomers and polyester elastomers, and any combinations of the above in the form of, for example, resin blends, polymer alloys or laminates.

It is preferable for the band 2 to be substantially transparent to ensure that the puncture site 510 is visible therethrough.

The material making up the band 2 is in the form of a sheet which may be of any suitable thickness. For the band 2 to have a tensile modulus and an elongation percentage within the subsequently described ranges, it is preferable for the sheet-like material of which it is made to have a thickness of about 0.1 to 0.5 mm, and especially about 0.2 to 0.3 mm.

The band 2 may have near the center thereof a curved plate holder 21 for holding the subsequently described curved plate 4. In the embodiment shown in FIG. 1, the curved plate holder 21 is composed in part of a separate strip-like member joined to the outside (or inside) surface of the band 2 by a suitable method such as welding (e.g., heat welding, high-frequency welding, ultrasonic welding) or adhesion (such as with an adhesive or solvent) so as to form a double layer construction. The curved plate 4 is inserted into a gap in the double layer and thereby held.

The band 2 has attached to it, on the inside surface (the front side in the plane of FIG. 1) thereof near the left end in FIG. 1, the male side (or female side) 31 of a surface fastener 3 such as a velcro-type hook and loop fastener (e.g., the product commonly known in Japan as Magic Tape®). Similarly, the band 2 has attached to it, on the outside surface (the back side in the plane of FIG. 1) near the right end in FIG. 1, the female side (or male side) 32 of a surface fastener 3. As shown in FIG. 2, the band 2 is attached to the wrist 500 by joining together the male side 31 and the female side 32 of this surface fastener 3. The means that may be employed to secure the band 2 in a wrapped state to the wrist 500 are not limited only to surface fasteners 3. Other suitable means include snaps, buttons, clips, and members such as buckles through which the ends of the band 2 are passed.

The curved plate 4 is inserted into the gap in the double layer construction of the curved plate holder 21 on the band 2, and is thereby held on the band 2.

The curved plate 4 is shaped so that at least a portion thereof is curved toward an inner peripheral side of the plate 4. This curved plate 4 is constructed of a material more rigid than the band 2 and maintains a substantially fixed shape.

As is apparent from FIG. 1, in this embodiment, the curved plate 4 has a shape that is elongated in the lengthwise direction of the band 2. As shown in FIG. 2, the curved plate 4 has a center portion 41 in the lengthwise direction thereof which is substantially uncurved and thus shaped as a flat plate. The curved plate 4 also has, on either side of this center portion 41, curved portions 42 which curve toward the inner peripheral side of the plate 4 and along the lengthwise direction of the band 2 (circumferential direction of the wrist 500). The curved portions 42 have a radius of curvature R2 which is smaller than the radius of curvature R1 of the center portion 41 (in the illustrated arrangement, R1 is substantially infinite).

The material making up the curved plate 4 is not subject to any particular limitation, as far as the puncture site 510 can be seen therethrough. Examples of materials of which the curved plate 4 may be made include acrylic resins, polyvinyl chloride (particularly rigid polyvinyl chloride), polyolefins such as polyethylene, polypropylene and polybutadiene, polystyrene, poly(4-methyl-1-pentene), polycarbonates, ABS resins, polymethyl methacrylate (PMMA), polyacetals, polyarylates, polyacrylonitriles, polyvinylidene fluorides, ionomers, acrylonitrile-butadiene-styrene polyesters such as polyethylene terephthalate (PET) and polybutylene terephthalate (PBT), butadiene-styrene copolymers, aromatic and aliphatic polyamides, and fluorocarbon resins such as polytetrafluoroethylene.

It is preferable for the curved plate 4 to be substantially transparent to ensure that the puncture site 510 is externally visible.

Alternatively, the curved plate 4 may have no uncurved portion such as center portion 41, and may thus be curved over its entire length.

The method of providing the curved plate 4 on the band 2 is not limited to the illustrated arrangement, and may involve joining the curved plate 4 to the inside surface or outside surface of the band 2 by a suitable method such as welding or adhesion. The band 2 need not encircle the wrist 500 completely. For example, another acceptable arrangement is one in which the band 2 is connected to both ends of the curved plate 4. It is thus not essential for a portion of the band 2 to overlap with the curved plate 4.

The band 2 or curved plate 4 has connected to the inner side thereof a balloon 5 made of a flexible material. The balloon 5 inflates when a fluid (a gas such as air, or a liquid) is introduced therein, thus applying pressure to the puncture site 510 on the wrist 500.

The balloon 5 is positioned near one end of the curved plate 4 in the lengthwise direction thereof. That is, in the arrangement shown in FIG. 2, the balloon 5 is in a position that overlaps with substantially the right half of the curved plate 4.

The material making up the balloon 5 is not subject to any particular limitation provided it is a material that allows the puncture site 510 to be seen. For example, a material similar to that making up the band 2 may be used. To facilitate joining of the balloon 5 with the band 2 by welding, and thus make the hemostatic device 1 easier to manufacture, it is preferable for the balloon 5 to be made of a material which is of the same nature or type as that making up the band 2.

It is desirable for the balloon 5 to be substantially transparent to ensure that the puncture site is externally visible.

The material making up the balloon 5 is in the form of a sheet which may be of any suitable thickness. For the balloon 5 to have a tensile modulus and an elongation percentage within the subsequently described ranges, it is preferable for the sheet-like material of which it is made to have a thickness of about 0.1 to 0.5 mm, and especially about 0.2 to 0.3 mm.

The balloon 5 may have a construction in which the edges of sheets made of the above-described material are sealed together by a suitable process such as welding or adhesion to form a sort of pouch. In the arrangement shown in FIG. 1, the balloon 5 is substantially square in the uninflated state.

The balloon 5 is connected to the band 2 by a flexible connector 11. In the present embodiment, the balloon 5 is connected to the band 2 by a connector 11 only on the side of one end of the curved plate 4; that is, only on the right side in FIG. 2. The connector 11 has a relatively short length, thereby keeping the balloon 5 tethered in a position deviated to one end of the curved plate 4. The connector 11 is preferably made of the same material as the balloon 5.

In the present embodiment, because only one side of the balloon 5 is connected to the band 2 by the connector 11, when the hemostatic device 1 is attached to the wrist 500 in the state shown in FIG. 2, the balloon 5 assumes a somewhat tilted orientation. As a result, the pressing force F applied to the puncture site 510 acts in an oblique direction.

As shown in FIG. 1, the balloon 5 has connected thereto an inflator 7 for introducing a fluid into the balloon 5. The inflator 7 is composed of a flexible tube 71 which is connected at a proximal end thereof to the balloon 5 and which has a lumen that communicates with the interior of the balloon 5, a bulb 72 which is provided at the distal end of the tube 71, and a tubular connector 73 which is joined to the bulb 72. The tube 71 may include a connector or other means (not shown) which is connected to the balloon 5 side thereof and adapted to allow the tube 71 to be detached from the hemostatic device 1 of the present invention.

Inflation of the balloon 5 is carried out by inserting the protruding tip of a syringe (not shown) into the connector 73 and pushing a plunger on the syringe so as to introduce fluid within the syringe through the inflator 7 into the balloon 5. Once fluid has been injected into the balloon 5 and the protruding tip of the syringe is withdrawn from the connector 73, a check valve within the connector 73 closes, preventing the fluid from leaking out and thus maintaining the balloon 5 in an inflated state.

As shown in FIG. 2, a secondary balloon 6 composed of a flexible material may be provided between the curved plate 4 and the above-described balloon 5 (sometimes referred to hereinafter as the "main balloon" to avoid confusion) in such a way that all or part of the secondary balloon 6 overlaps with the main balloon 5. This secondary balloon 6 functions as a pressing member for pressing against the main balloon 5.

Under the pressure of the fluid with which it is filled, the secondary balloon 6 applies to the main balloon 5 a pressing force (arrow f in FIG. 2) which is directed toward substantially the center 520 of the wrist 500. Under the influence of this pressing force f from the secondary balloon 6, the main balloon 5 in turn applies to the puncture site 510 a compressive force (arrow F in FIG. 2) that acts in an oblique or inclined direction (toward the center 520 of the wrist 500) rather than vertically downward (that is, in a vertical direction with respect to the surface of the wrist 500). This arrangement provides a better hemostatic effect and is thus able to more reliably stop bleeding than when compression is applied to the puncture site 510 in a vertically downward direction.

In the arrangement illustrated in FIG. 2 in which the hemostatic device 1 is shown wrapped about the wrist 500, the main balloon 5 is not in contact with the curved plate 4 through the band 2. However, a portion of the main balloon 5 may be in contact with the curved plate 4 through the band 2.

The material making up the secondary balloon 6 is not subject to any particular limitation, as far as the puncture site 510 can be seen therethrough. For example, materials similar to the above-described materials making up the band 2 and the main balloon 5 may be used. It is preferable for the secondary balloon 6 to be substantially transparent to ensure that the puncture site 510 is externally visible. The material making up the secondary balloon 6 is in the form of a sheet which may have a thickness like that of the material making up the main balloon 5. The secondary balloon 6 may also have a construction like that of the main balloon 5.

In the present embodiment of the invention, the secondary balloon 6 has a smaller width in the lengthwise direction of the band 2 than the main balloon 5. Hence, the secondary balloon 6 is smaller in size than the main balloon 5 and thus applies pressure locally to the main balloon 5. This enables the direction of the pressing force F applied by the main balloon 5 to the puncture site 510 to be more reliably inclined.

Moreover, the secondary balloon 6 is positioned near the right end of the curved plate 4 in the lengthwise direction thereof, as shown in FIG. 2. This enables the pressing force f applied by the secondary balloon 6 to the main balloon 5 to be made more reliably directed toward the center 520 of the wrist 500. In turn, the direction of the pressing force F applied by the main balloon 5 to the puncture site 510 can be more reliably inclined.

In this embodiment, as mentioned above, the curved plate 4 has, on the side on which the main balloon 5 is positioned (the right side in FIG. 2), a curved portion 42 with a radius of curvature smaller than that of the center portion 41 of the curved plate 4. The secondary balloon 6 contacts, through the band 2, the curved portion 42 of the curved plate 4 or a portion to the right side thereof in FIG. 2. In this way, the direction of the force incurred by the secondary balloon 6 from the curved plate 4, i.e., the normal direction of the curved plate 4 where it contacts the secondary balloon 6 through the band 2, is inclined toward the center 520 of the wrist 500. As a result, the directions of pressing force f and pressing force F can be more reliably inclined.

In this embodiment, a portion of the main balloon 5 and a portion of the secondary balloon 6 are joined together by a suitable method such as welding or adhesion. At the resulting junction, an opening 12 is formed as a means for communicating between the interior of the main balloon 5 and the interior of the secondary balloon 6. When a fluid is injected into the main balloon 5 in the manner described above, some of the injected fluid flows through the opening 12 into the secondary balloon 6, so that the secondary balloon 6 inflates as the main balloon 5 inflates. In this way, both balloons can be inflated in a single operation, providing excellent ease of use and efficiency.

In addition to being joined to the main balloon 5 in the vicinity of the opening 12, the secondary balloon 6 may also be joined to the main balloon 5 at a place near the connector 11 (on the right end in FIG. 2). This enables pressure to be more reliably applied to the main balloon 5 and increases the upward pushing force upon the curved plate 4, making it easier to move the curved plate 4 away from the wrist 500.

In a different arrangement than that shown in FIGS. 1 and 2, inflation of the secondary balloon 6 by the introduction of a fluid may be carried out separately from inflation of the main balloon 5.

Moreover, the secondary balloon 6 need not be adapted to inflate with the injection of a fluid at the time of use as in the present embodiment. Instead, it may be filled with a fluid and inflated to begin with; that is, prior to the time of use.

In this invention, the pressing member which presses against the main balloon 5 is not limited to a secondary balloon 6. Other types of pressing members that may be used for this purpose include pads made of a spongy substance, an elastomeric material, an assemblage of fibers such as cotton, or combinations thereof.

A method of using the above-described hemostatic device 1 of the invention is described below.

(1) Before attaching the hemostatic device 1 to a patient's limb, the main balloon 5 and the secondary balloon 6 are placed in an uninflated state. In cases where the procedure is carried out at the wrist 500, the site of puncture 510 into an artery is generally on the inner side of the wrist 500 (where the tendons are located) and on the thumb side. There will be times where an introducer sheath (not shown) is inserted and in place at the puncture site 510, and other times where no such sheath is present. The method of using the inventive hemostatic device 1 is the same in both cases. While compressing the puncture site 510 with a finger or other suitable means, the operator positions the main balloon 5 over the puncture site 510, wraps the band 2 around the wrist 500, and secures, or joins, the band 2 near both ends thereof with a surface fastener 3.

In a method of using the hemostatic device 110 according to the subsequently described fourth embodiment of the invention, the operator typically wraps the band 2 around a wrist 500 where an introducer sheath may or may not be inserted and in place, positions the main balloon 5 (band 2) so that a marker 8 provided on the balloon 5 lies over the puncture site 510, and secures, or joins, the band 2 near both ends thereof with a surface fastener 3.

(2) Once the hemostatic device 1 has been attached to the wrist 500, a syringe (not shown) is connected to the connector 73 on the inflator 7 and a fluid is introduced into the main balloon 5 and the secondary balloon 6 as described above, thereby inflating the main balloon 5 and the secondary balloon 6. In the present invention, the degree of inflation by the main balloon 5 and the secondary balloon 6, i.e., the compressive force applied to the puncture site 510, can easily be adjusted for the particular medical case and circumstances by varying the amount of fluid introduced at this time, making operation of the hemostatic device 1 very easy and efficient.

(3) Once the main balloon 5 and the secondary balloon 6 have been inflated, the syringe is separated from the connector 73. If an introducer sheath is in place at the puncture site 510, it is removed at this point.

If the connector 73 has a check valve, the check valve is closed after the syringe is removed, which will prevent the sudden leakage of fluid. Thus, the main balloon 5 and the secondary balloon 6 remain inflated and so compression against the puncture site 510 is maintained (see FIG. 2). In this state, the main balloon 5 applies pressure locally to the puncture site 510 and its environs. Moreover, inflation of the main balloon 5 and the secondary balloon 6 causes the curved plate 4 to move away from the surface of the wrist 500 so that it does not readily come into contact with the wrist 500. Accordingly, compressive forces are concentrated at the puncture site 510 and its environs, resulting in an excellent hemostatic effect while avoiding the compression of other tissues, including blood vessels not requiring hemostasis and nerves, and thus effectively preventing undesirable effects such as numbness of the hand and poor circulation.

(4) In the fifth embodiment of the invention described later in this specification, after inflation of the main balloon 5 is complete, the internal pressure of the balloon 5 gradually decreases. The internal pressure 60 minutes after inflation falls to about 20 to 70% of the initial internal pressure. As a result, the compressive force applied to the puncture site 510 eases over time, making it possible to prevent the harmful effects of a sustained compressive force, such as numbness, pain, and the occlusion of blood vessels (poor blood circulation).

(5) When bleeding is determined to have stopped to a sufficient degree, the hemostatic device 1 of the invention is removed from the puncture site 510. The length of time from the completion of balloon 5 inflation until removal of the hemostatic device 1 (referred to hereinafter as the "hemostatic device attachment time") is not subject to any particular limitation. Hemostasis using this device may be carried out for a period of, for example, 150 to 360 minutes. The hemostatic device attachment time may be selected as appropriate for the individual patient and his or her medical condition.

Second to fifth embodiments of the inventive hemostatic device are described below in conjunction with the attached drawings, with particular reference to those features which differ from the foregoing first embodiment of the invention. Descriptions of like features are omitted.

Second Embodiment

Figure 3:
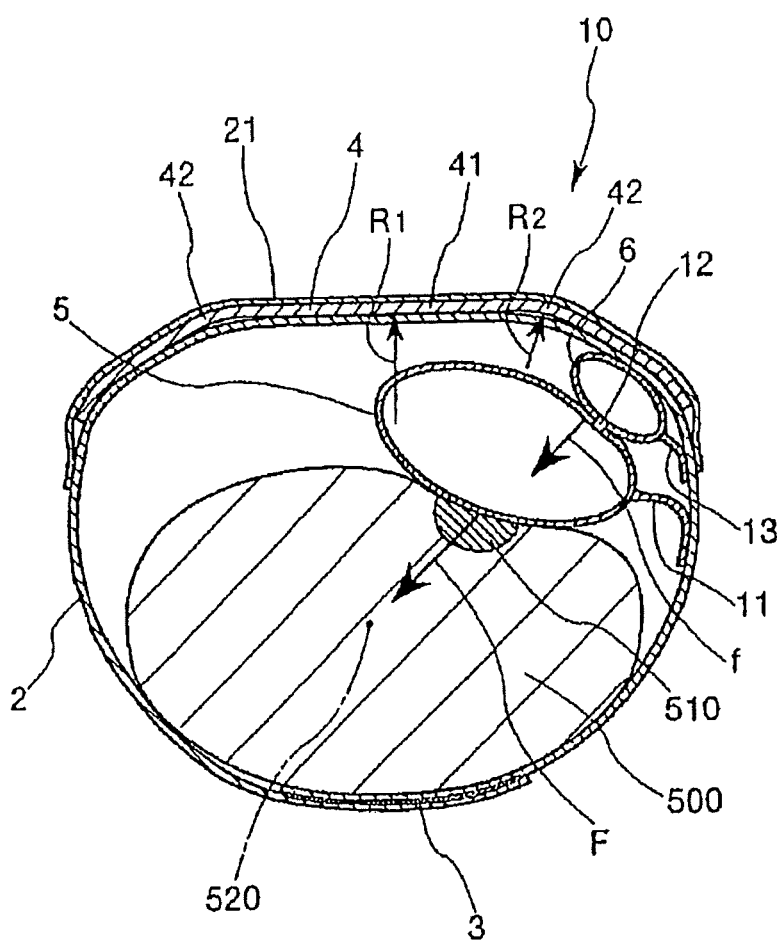
FIG. 3 is a sectional view showing a second embodiment of the hemostatic device according to the invention.

FIG. 3 is a sectional view showing a hemostatic device according to a second embodiment of the invention during use.

The hemostatic device 10 in this embodiment has the same features as the hemostatic device 1 in the above-described first embodiment, except that the secondary balloon 6 is connected to the band 2 via a flexible connector 13.

In the present embodiment, the secondary balloon 6, by being connected to the band 2 via a connector 13 on the same side as the connector 11 for the main balloon 5 (i.e., the right side in FIG. 3), more easily and reliably assumes a tilted orientation. This more readily allows the pressing force f applied to the main balloon 5 to act in an oblique direction (that is, in a direction which causes the main balloon 5 to face substantially the center 520 of the wrist 500), thus enabling a better hemostatic effect to be achieved.

Third Embodiment

Figure 4:
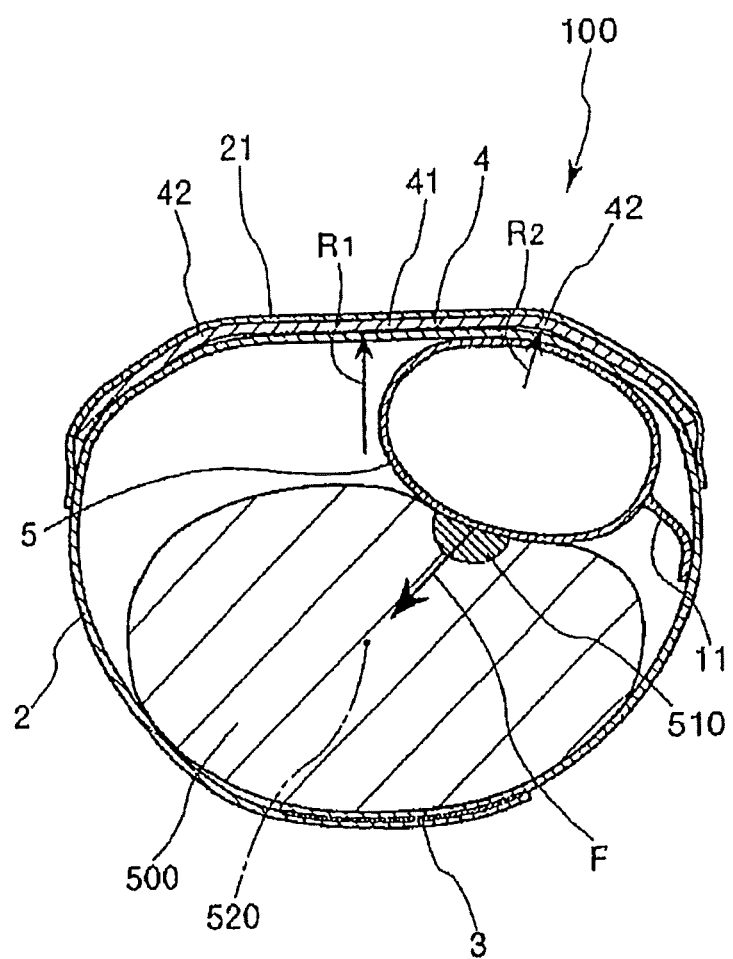
FIG. 4 is a sectional view showing a third embodiment of the hemostatic device according to the invention.

FIG. 4 is a sectional view showing a hemostatic device according to a third embodiment of the invention during use.

The hemostatic device 100 in this embodiment has the same features as the above-described first embodiment, except that it lacks a secondary balloon 6.

That is, in the present embodiment, there is no secondary balloon 6. Instead, the main balloon 5 comes into contact with the curved plate 4 through the band 2. Moreover, the balloon 5 is connected to the band 2 only on one side through a connector 11, thus giving the balloon 5 a somewhat tilted orientation, as shown in FIG. 4. This enables the compression force F applied to the puncture site 510 to act in an oblique direction (that is, in a direction facing the center 520 of the wrist 500). As in the first embodiment described above, the result is that a better hemostatic effect can be obtained.

Moreover, as in the first embodiment, the balloon 5 is positioned on the connector 11 side (the right side in FIG. 4) with respect to the curved plate 4. The curved plate 4 has a center portion 41 and, on the side on which the balloon 5 is positioned (the right side in FIG. 4), a curved portion 42 with a smaller radius of curvature than the center portion 41. On the right side (in FIG. 4) of the curved portion 42, the curved plate 4 pushes the balloon 5 (through the intervening band 2) in a direction facing the center portion 520 of the wrist 500. Hence, in this embodiment, the compressive force F acts more reliably in an oblique direction.

Fourth Embodiment

Figure 5:
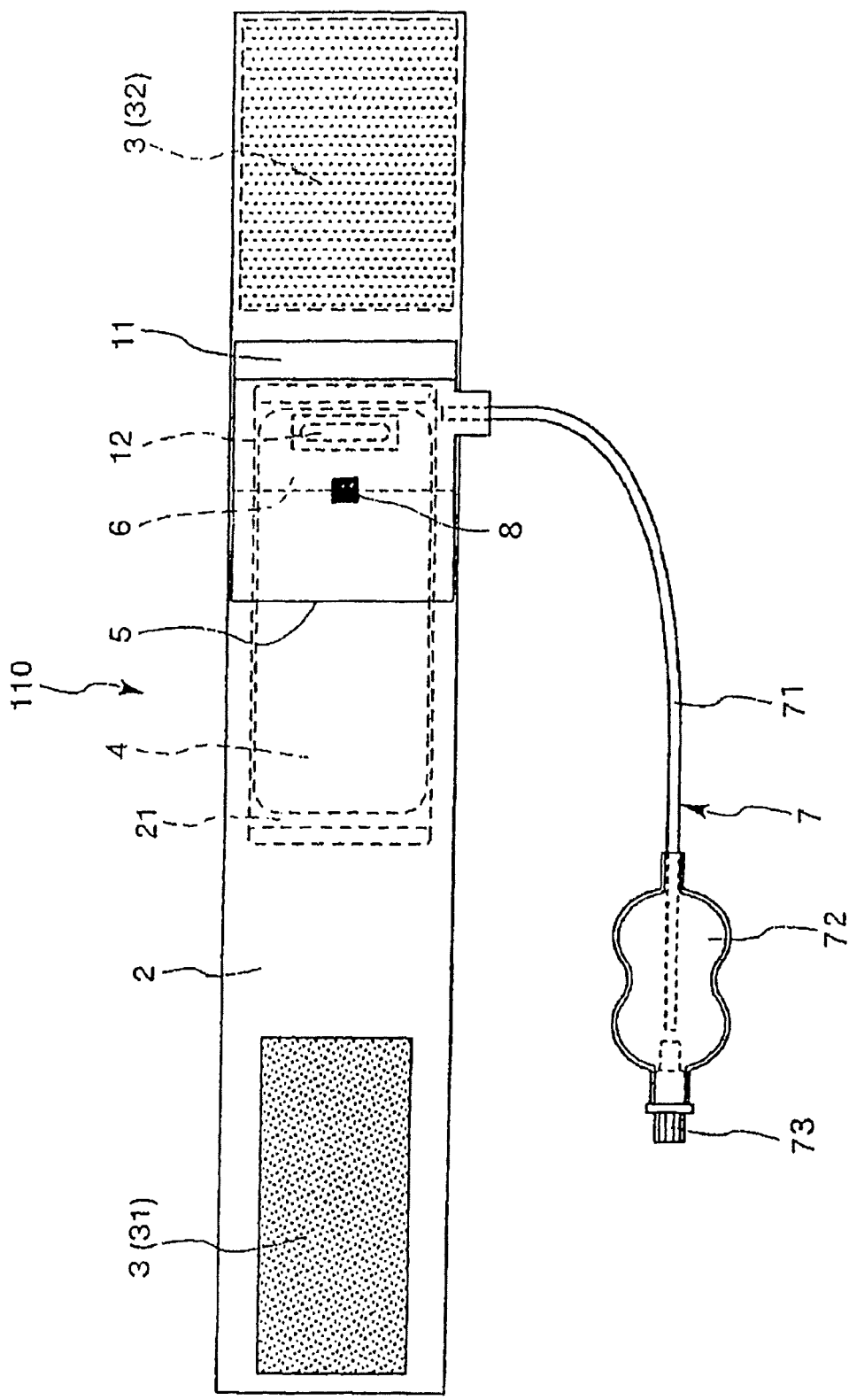
FIG. 5 is a bottom view of a fourth embodiment of the hemostatic device according to the invention. This shows the side of the device that serves as the inside surface when the device is attached to the wrist of a patient.
Figure 6:
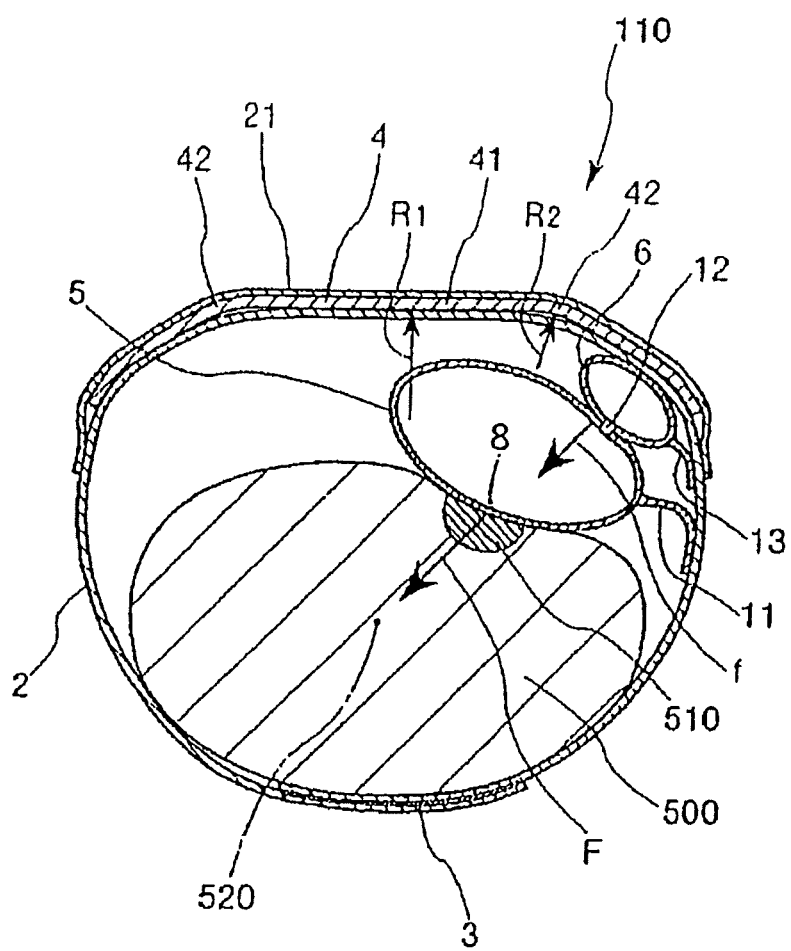
FIG. 6 is a sectional view showing the same hemostatic device as in FIG. 5 during use.

FIG. 5 is a bottom view of a fourth embodiment of the hemostatic device of the invention. This shows the side of the device that serves as the inside surface when the device is attached to the wrist of a patient. FIG. 6 is a sectional view showing the same hemostatic device as in FIG. 5 when attached and in use on the wrist of a patient.

As shown in FIG. 5, the hemostatic device 110 of the present embodiment has a marker 8 provided on the inside surface of the main balloon 5; that is, the surface which comes into contact with the puncture site 510 (the front side in the plane of FIG. 5). Providing such a marker 8 on the balloon 5 in the hemostatic device 110 of this embodiment facilitates proper positioning of the balloon 5 at the puncture site 510, which in turn helps prevent blood leakage and hematoma formation due to poor positioning of the balloon 5.

As shown in FIG. 5, it is preferable for the marker 8 to be provided at the center of the balloon 5; that is, to be centered at the intersection of the diagonals for the square shape of the balloon 5. Because this enables the center of the balloon 5 to be properly positioned at the puncture site 510, when the balloon 5 has been inflated, the compressive force applied by the balloon 5 acts reliably upon the puncture site 510.

The marker 8 is not limited to any particular shape. Examples of suitable shapes include circular, triangular and square shapes. In FIG. 5, the marker 8 has a square shape.

No particular limitation is imposed on the size of the marker 8. However, when the marker 8 is square, for example, it is preferable for the length of one side of the square to be in a range of 1 to 4 mm. If the length of one side is 5 mm or more, the marker 8 becomes large relative to the size of the puncture site 510, which may make the center of the balloon 5 difficult to position properly over the puncture site 510.

The marker 8 may be made of any suitable material, including oil-based coloring materials such as inks, and pigment-containing resins.

The color of the marker 8 is not subject to any particular limitation, insofar as it is a color that enables the balloon 5 to be properly positioned at the puncture site 510. However, a greenish color is preferred because this makes the marker 8 readily visible on blood and the skin, thus enabling the balloon 5 to be more easily positioned at the puncture site 510.

It is also desirable for the marker 8 to be translucent so as to enable the puncture site 510 to be visible from outside of the marker 8.

No particular limitation is imposed on the method used to place the marker 8 on the balloon 5. Examples of suitable methods include printing the marker 8 onto the balloon 5, welding the marker 8 to the balloon 5, and applying an adhesive to one side of the marker 8 and affixing it to the balloon 5.

It is also possible to place the marker 8 on the outside surface of the balloon 5; that is, on the side opposite the surface of the balloon 5 that comes into direct contact with the puncture site 510 (the back side in the plane of FIG. 5).

Alternatively, instead of being placed on the main balloon 5, the marker 8 may be placed on the band 2, on the curved plate 4, or on the subsequently described secondary balloon 6. In such cases, it is advantageous for the marker 8 to be placed in such a way that it can be positioned over the center of the main balloon 5.

In the hemostatic device 110 of the present embodiment, the band 2 should be made of a material which allows the puncture site 510 to be seen. Those materials mentioned earlier in connection with the band in the first embodiment of the hemostatic device are widely used for the material of the band 2 in this embodiment. Further, it is preferable for the band 2 to be substantially transparent so that the puncture site 510 can be reliably seen from the outside and the marker 8 can be easily and properly positioned at the puncture site 510.

In the hemostatic device 110 of this embodiment, the curved plate 4 should be made of a material which allows the puncture site 510 to be seen. Those materials mentioned earlier in connection with the curved plate in the first embodiment of the hemostatic device are widely used for the material of the curved plate 4 in this embodiment. Further, it is preferable for the curved plate 4 in the present embodiment to be substantially transparent so that the puncture site 510 is reliably visible from the outside and the marker 8 can be easily and properly positioned at the puncture site 510.

In the hemostatic device 110 of this embodiment, the main balloon 5 should be made of a material which allows the puncture site 510 to be seen. Those materials mentioned earlier in connection with the main balloon in the first embodiment of the hemostatic device are widely used for the material of the main balloon 5 in this embodiment. Further, it is desirable for the main balloon 5 to be substantially transparent so that the puncture site 510 is reliably visible from the outside and the marker 8 can be easily and properly positioned at the puncture site 510.

In the hemostatic device 110 of this embodiment, the second balloon 6 should be made of a material which allows the puncture site 510 to be seen. Those materials mentioned earlier in connection with the second balloon in the first embodiment of the hemostatic device are widely used for the material of the second balloon 6 in this embodiment. Further, it is preferable for the secondary balloon 6 to be substantially transparent so that the puncture site 510 is reliably visible from the outside and the marker 8 can be easily and properly positioned at the puncture site 510. By adopting an arrangement in which, as shown in FIG. 6, the secondary balloon 6 is connected to the band 2 through a connector 13 on the same side (the right side in FIG. 6) as the connector 11 for the main balloon 5, the same effect can be achieved as in the second embodiment described earlier.

Fifth Embodiment

In the hemostatic device of the present embodiment, the balloon 5 is constructed so that, following complete inflation thereof, the internal pressure decreases over time, the internal pressure 60 minutes after inflation becoming 20 to 70%, and preferably 30 to 60%, of the initial internal pressure. Here, "initial internal pressure" refers to the pressure within the balloon 5 ten seconds after inflation is complete; that is, after the balloon 5 has been inflated to a degree sufficient to achieve a compressive force suitable to stop bleeding.

By means of such an arrangement, the compressive force applied by the balloon 5 relaxes suitably (neither too much nor too little) with the passage of time, making it possible to effectively prevent the harmful effects of a sustained compressive force, such as numbness, pain and vascular blockage (poor circulation) at the puncture site 510 and areas peripheral thereto. In particular, the decrease in the internal pressure of the balloon 5 occurs spontaneously without requiring some sort of manual operation (such as the loosening of a valve to reduce pressure or release gas) by a physician, nurse or other health care practitioner. This makes it possible to avoid the trouble and inconvenience associated with such operations.

If the internal pressure 60 minutes after balloon inflation exceeds 70% of the initial internal pressure, the compressive force (internal pressure) at the time of inflation of the balloon 5 remains at substantially the same level. There may be situations in which it may be desirable to avoid such a case.

On the other hand, if the internal pressure 60 minutes after balloon inflation is less than 20% of the initial internal pressure, the percent decrease in the internal pressure of the balloon 5 may be more than desired. There may be situations in which such decrease in the internal balloon pressure causes the compressive force of the balloon 5 to diminish before sufficient hemostasis has occurred, which may result in blood leakage at the puncture site 510.

Specific arrangements for lowering the internal pressure of the balloon 5 over time in the manner described above are given below.

A. Make the band 2 and/or the balloon 5 of a material which is flexible and easily deformed (extended).

The band 2 and/or balloon 5 gradually deform under the internal pressure and resilience of the inflated balloon 5 so as to conform to the shape of the puncture site 510. As a result, the internal pressure of the balloon 5 decreases, easing the compressive force applied to the puncture site 510. That is, the decrease in the compressive force acting upon the puncture site 510 is controlled by the physical properties (tensile modulus, thickness, elongation percentage, etc.) of the materials making up the band 2 and/or balloon 5.

Specifically, the band 2 has a tensile modulus of preferably not more than 10 gf/mm$^2$, and most preferably 2 to 9 gf/mm$^2$.

The band 2 wrapped around the wrist 500 has an elongation percentage 180 minutes after balloon inflation of preferably 1 to 7%, and more preferably 3 to 6%.

B. Control the gas permeability of the balloon 5. This enables gas within the balloon 5 to pass through the sheet material making up the balloon 5 and be slowly released to the exterior. As a result, the internal pressure of the balloon 5 gradually decreases, easing the compressive force applied to the puncture site 510.

C. Control the gas permeability of the secondary balloon 6 which communicates with the main balloon 5. The gas within the secondary balloon 6 passes through the sheet material of which the secondary balloon 6 is made and is gradually released to the exterior. This brings about a gradual decline in the internal pressure of both the secondary balloon 6 and also the main balloon 5 that communicates with it, easing the compressive force applied to the puncture site 510.

D. Control the gas permeability of the tube 71 which communicates with the balloon 5 and/or the bulb 72. In this way, the gas within the balloon 5 passes through the tube 71 and/or bulb 72 and is slowly released to the exterior, allowing the internal pressure of the balloon 5 to gradually decrease and thus easing the compressive force applied to the puncture site 510.

E. Make the gas backflow-preventing effect of the check valve within the connector 73 incomplete so that a small amount of gas leaks out through the check valve. As a result, a small amount of gas within the balloon 5 is steadily discharged to the exterior through the check valve within the connector 73, gradually lowering the internal pressure of the balloon 5 and easing the compressive force applied to the puncture site 510.

F. Combinations of any two or more of above arrangements A to E.

Methods A to F above have the advantage of enabling control of the interior pressure within the balloon 5 (i.e., pressure reduction over time) to be achieved with a simple arrangement. Method A in particular enables the interior pressure of the balloon 5 to be controlled by suitable selection of the constituent materials and dimensions of the band 2 and the balloon 5.

In the hemostatic device of the present embodiment, the internal pressure of the balloon 5 gradually decreases shortly after inflation has been completed. The internal pressure 60 minutes after dilation falls to about 20 to 70% of the initial internal pressure. This eases the compressive force applied to the puncture site 510, making it possible to prevent various harmful effects due to the sustained application of a compressive force, such as numbness, pain and vascular blockage (poor circulation).

Once it is determined that sufficient hemostasis has been achieved, the hemostatic device is removed from the puncture site 510. The time until removal of the hemostatic device following complete inflation of the balloon (i.e., the hemostatic device attachment time) is not subject to any particular limitation, although removal is typically carried out after about 150 to 360 minutes. This hemostatic device attachment time can be selected as appropriate for the particular patient and his or her condition.

EXAMPLES

Examples of the invention and comparative examples are given below by way of illustration and not by way of limitation.

Example 1

A main balloon and a secondary balloon were each fabricated from a substantially transparent polyvinyl chloride sheet having a tensile modulus of 8 gf/mm$^2$ and a thickness of 0.3 mm. In addition, a band was fabricated from a substantially transparent polyvinyl chloride sheet also having a tensile modulus of 8 gf/mm$^2$ and a thickness of 0.3 mm. The band had a length of 190 mm and a width of 40 mm. The main balloon, secondary balloon and band were welded together at the necessary places to form a hemostatic device according to the fifth embodiment of the invention having the construction shown in FIG. 1. A curved plate made of substantially transparent polycarbonate resin and curved at both ends was inserted into a curved plate holder on the band.

Figure 7:
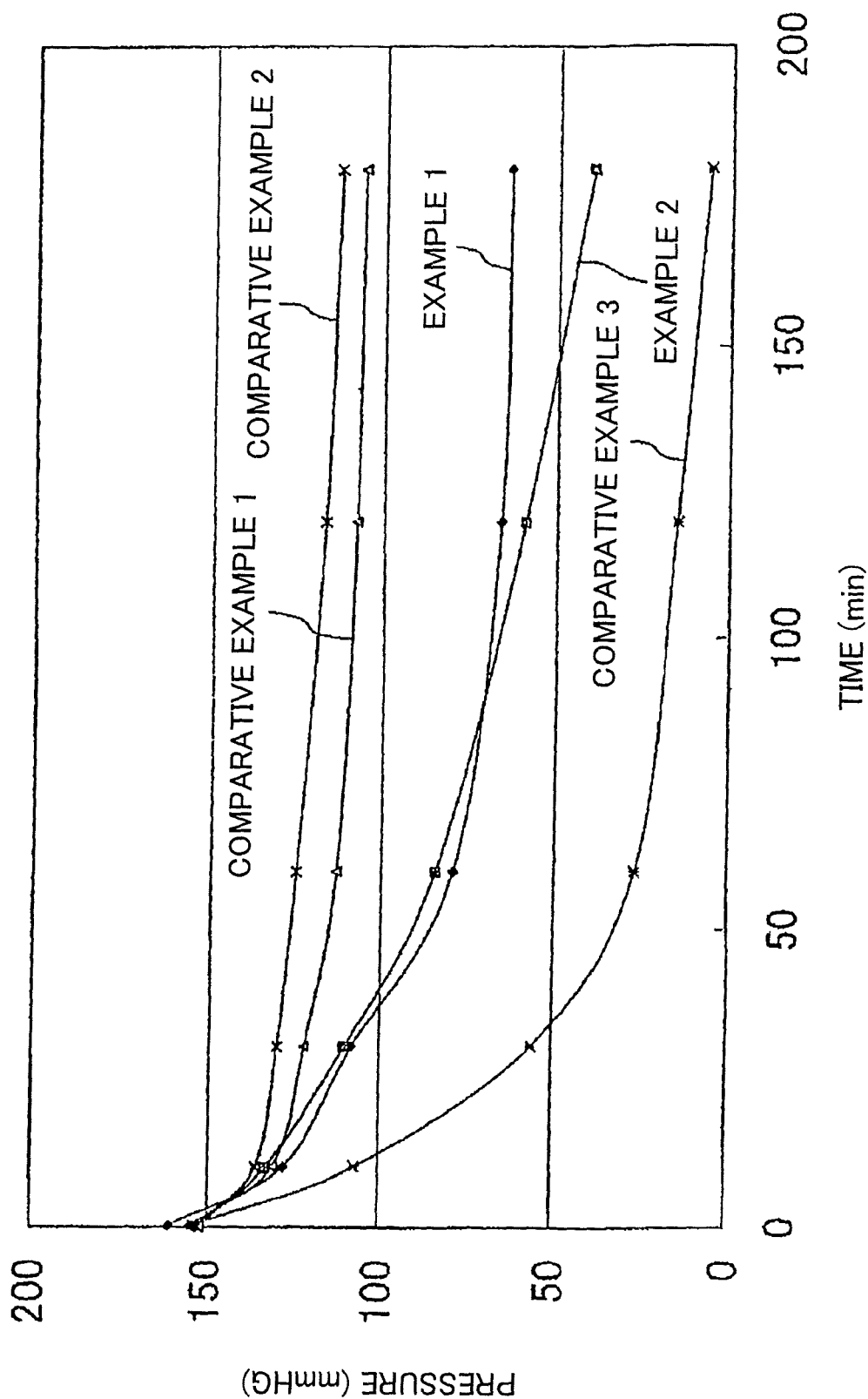
FIG. 7 is a graph of the change over time in balloon internal pressure in the examples of the invention and the comparative examples which are described later in this specification.

This hemostatic device was wrapped around the wrist and the balloon was inflated by injecting air into the balloon through the connector 73 on the inflator 7 until the balloon internal pressure reached about 150 mmHg. Next, the internal pressure of the balloon was measured, first 10 seconds after full inflation of the balloon (initial internal pressure), then 10, 30, 60, 120 and 180 minutes after full inflation. The results of measurement are shown in Table 1 below and FIG. 7.

In addition, 180 minutes after inflation, the hemostatic device was removed from the wrist and the length of the band was measured. The band had a length of 197 mm, representing an elongation percentage of 3.6%.

TABLE 1

| | Example 1 | |
|---|---|---|
| Time elapsed after balloon inflation | Internal pressure of balloon (mmHg) | Pressure as a percentage of initial internal pressure |
| 10 seconds | 161 | 100 |
| 10 minutes | 128 | 79.5 |
| 30 minutes | 108 | 67.0 |
| 60 minutes | 79 | 49.0 |
| 120 minutes | 66 | 40.9 |
| 180 minutes | 64 | 39.7 |

Example 2

A main balloon and a secondary balloon were each fabricated from a substantially transparent polyvinyl chloride sheet material having a tensile modulus of 3 gf/mm$^2$ and a thickness of 0.2 mm. In addition, a band was fabricated from a substantially transparent polyvinyl chloride sheet material also having a tensile modulus of 3 gf/mm$^2$ and a thickness of 0.2 mm. The band had a length of 190 mm and a width of 40 mm. The main balloon, secondary balloon and band were welded together at the necessary places to form a hemostatic device according to the fifth embodiment of the invention having the construction shown in FIG. 1. A curved plate made of substantially transparent polycarbonate resin and curved at both ends was inserted into a curved plate holder on the band.

This hemostatic device was wrapped around the wrist and the balloon was inflated by injecting air into the balloon through the connector 73 on the inflator 7 until the balloon internal pressure reached about 150 mmHg. Next, the internal pressure of the balloon was measured, first 10 seconds after full inflation of the balloon (initial internal pressure), then 10, 30, 60, 120 and 180 minutes after full inflation. The results of measurement are shown in Table 2 below and FIG. 7.

In addition, 180 minutes after inflation, the hemostatic device was removed from the wrist and the length of the band was measured. The band had a length of 201 mm, representing an elongation percentage of 5.8%.

TABLE 2

Example 2

| Time elapsed after balloon inflation | Internal pressure of balloon (mmHg) | Pressure as a percentage of initial internal pressure |
|---|---|---|
| 10 seconds | 152 | 100 |
| 10 minutes | 133 | 87.5 |
| 30 minutes | 110 | 72.4 |
| 60 minutes | 84 | 55.2 |
| 120 minutes | 59 | 38.8 |
| 180 minutes | 40 | 26.3 |

Comparative Example 1

A main balloon and a secondary balloon were each fabricated from a substantially transparent polyvinyl chloride sheet material having a tensile modulus of 16 gf/mm$^2$ and a thickness of 0.3 mm. In addition, a band was fabricated from a substantially transparent polyvinyl chloride sheet material having a tensile modulus of 17 gf/mm$^2$ and a thickness of 0.5 mm. The band had a length of 190 mm and a width of 40 mm. The main balloon, secondary balloon and band were welded together at the necessary places to form a hemostatic device having the construction shown in FIG. 1. A curved plate made of substantially transparent polycarbonate resin and curved at both ends was inserted into a curved plate holder on the band.

This hemostatic device was wrapped around the wrist and the balloon was inflated by injecting air into the balloon through the connector 73 on the inflator 7 until the balloon internal pressure reached about 150 mmHg. Next, the internal pressure of the balloon was measured, first 10 seconds after full inflation of the balloon (initial internal pressure), then 10, 30, 60, 120 and 180 minutes after full inflation. The results of measurement are shown in Table 3 below and FIG. 7.

In addition, 180 minutes after inflation, the hemostatic device was removed from the wrist and the length of the band was measured. The band had a length of 191 mm, representing an elongation percentage of 0.5%.

TABLE 3

Comparative Example 1

| Time elapsed after balloon inflation | Internal pressure of balloon (mmHg) | Pressure as a percentage of initial internal pressure |
|---|---|---|
| 10 seconds | 155 | 100 |
| 10 minutes | 131 | 84.5 |
| 30 minutes | 122 | 78.7 |
| 60 minutes | 113 | 73.9 |
| 120 minutes | 108 | 69.6 |
| 180 minutes | 106 | 68.3 |

Comparative Example 2

A hemostatic device manufactured by Nippon Sherwood Medical Industries Ltd. under the trade name Radiseal was furnished for use. In this hemostatic device, the band was composed of a polyvinyl chloride sheet having a thickness of about 0.5 mm and the balloon was composed of a polyvinyl chloride sheet having a thickness of about 0.3 mm.

The device lacked a secondary balloon and was constructed such that, when inflated, the balloon pressed against substantially the center of the wrist.

This hemostatic device was wrapped around the wrist and the balloon was inflated by introducing air from an inflator until the balloon internal pressure reached about 150 mmHg. Next, the internal pressure of the balloon was measured, first 10 seconds after full inflation of the balloon (initial internal pressure), then 10, 30, 60, 120 and 180 minutes after full inflation. The results of measurement are shown in Table 4 below and FIG. 7.

TABLE 4

Comparative Example 2

| Time elapsed after balloon inflation | Internal pressure of balloon (mmHg) | Pressure as a percentage of initial internal pressure |
|---|---|---|
| 10 seconds | 153 | 100 |
| 10 minutes | 136 | 88.8 |
| 30 minutes | 130 | 84.9 |
| 60 minutes | 125 | 81.6 |
| 120 minutes | 117 | 76.4 |
| 180 minutes | 113 | 73.8 |

Comparative Example 3

A main balloon and a secondary balloon were each fabricated from a substantially transparent polyvinyl chloride sheet material having a tensile modulus of 16 gf/mm$^2$ and a thickness of 0.3 mm. In addition, a band was fabricated from a substantially transparent polyvinyl chloride sheet material having a tensile modulus of 17 gf/mm$^2$ and a thickness of 0.5 mm. The band had a length of 190 mm and a width of 40 mm. The main balloon, secondary balloon and band were welded together at the necessary places. In addition, the sheet material making up the secondary balloon was pierced in three places with a needle to form small holes and thereby increase the gas permeability of the secondary balloon. This yielded a hemostatic device having the construction shown in FIG. 1. A curved plate made of substantially transparent polycarbonate resin and curved at both ends was inserted into a curved plate holder on the band.

This hemostatic device was wrapped around the wrist and the balloon was inflated by injecting air into the balloon through the connector 73 on the inflator 7 until the balloon internal pressure reached about 150 mmHg. Next, the internal pressure of the balloon was measured, first 10 seconds after full inflation of the balloon (initial internal pressure), then 10, 30, 60, 120 and 180 minutes after full inflation. The results of measurement are shown in Table 5 below and FIG. 7.

TABLE 5

Comparative Example 3

| Time elapsed after balloon inflation | Internal pressure of balloon (mmHg) | Pressure as a percentage of initial internal pressure |
| --- | --- | --- |
| 10 seconds | 154 | 100 |
| 10 minutes | 107 | 69.5 |
| 30 minutes | 56 | 36.4 |
| 60 minutes | 27 | 17.5 |
| 120 minutes | 15 | 9.7 |
| 180 minutes | 6 | 3.9 |

In both Examples 1 and 2 according to the invention, no numbness, pain or poor circulation arose in the wrist or areas peripheral thereto, such as the palm and fingers, when the hemostatic device was attached or even later when the hemostatic device was removed from the wrist 180 minutes after inflation of the balloon.

By contrast, in Comparative Examples 1 and 2, some numbness of the fingers was sensed when the hemostatic device was attached and when the hemostatic device was removed from the wrist 120 minutes or 180 minutes after inflation of the balloon.

In Comparative Example 3, a sense of pressure by the balloon at the wrist ceased almost entirely to be felt 30 to 60 minutes after balloon inflation. The hemostatic effects were thus presumably insufficient in this case.

The illustrated embodiments of the hemostatic device of the invention have been described above, although many modifications and variations may be made thereto in light of the above teachings. It is therefore to be understood that the invention may be practiced otherwise than as specifically described without departing from the scope of the appended claims. For example, various parts of the hemostatic device having the specific configurations shown and described herein may be substituted with parts of similar function but having other configurations. Moreover, other suitable components may be added to the hemostatic device as described herein.

The hemostatic device of the invention is not limited to use on the wrist alone, and can be employed as a hemostatic device for attachment and use on any portion of a patient's arm or leg (referred to collectively in this specification as "limbs").

As described above and demonstrated in the examples, the hemostatic device of the invention provides excellent hemostatic effects and moreover prevents harmful effects such as numbness and poor circulation in areas peripheral to the site of attachment thereof.

An even better hemostatic effect can be obtained when the balloon is in a position deviated to one end of the curved plate in the lengthwise direction of the band, and especially when the curved plate has, on the side on which the balloon is positioned, a portion with a smaller radius of curvature than the center portion of the curved plate.

By providing a marker for positioning the balloon at the site where bleeding is to be stopped, the balloon can easily be properly positioned and blood leakage or hematoma formation due to incorrect placement of the balloon can be prevented.

In embodiments of the inventive hemostatic device in which the internal pressure of the inflated balloon decreases over time, the compressive force applied by the balloon relaxes suitably (neither too much nor too little) with the passage of time, enabling the effective prevention of harm from a sustained compressive force, such as numbness, pain or vascular blockage (poor circulation) at the puncture site and areas peripheral thereto.

In such embodiments, the decrease in the internal pressure of the balloon occurs spontaneously without requiring some sort of manual operation (such as the loosening of a valve to reduce pressure or release gas) by a physician, nurse or other health care practitioner. This makes it possible to avoid the trouble and inconvenience associated with such operations.

What is claimed is:

1. A hemostatic device to stop bleeding at a puncture site on a limb of a patient, the hemostatic device comprising:
a flexible band portion and a more rigid portion, the flexible band portion being configured to be wrapped around at least a portion of the limb of the patient to apply the hemostatic device to the limb of the patient, the more rigid portion and the flexible band portion possessing an inner side that faces toward the limb of the patient when the hemostatic device is applied to the patient's limb;
an inflatable balloon that inflates when a fluid is introduced into the inflatable balloon, the inflatable balloon being positioned to contact a surface of the patient's limb when the inflatable balloon is inflated while the hemostatic device is applied to the limb of the patient, the inflatable balloon including a center;
the inner side of the more rigid portion comprising a curved inner side part that is curved;
a marker positioned in alignment with the center of the inflatable balloon to facilitate positioning the hemostatic device when applying the hemostatic device to the limb of the patient so that when the hemostatic device is applied to the limb of the patient the marker overlies the puncture site;
the inflatable balloon being located at the inner side of the more rigid portion so that the inflatable balloon is between the inner side of the more rigid portion and the limb of the patient when the hemostatic device is applied to the limb of the patient;
the inflatable balloon being positioned relative to the curved inner side part of the more rigid portion such that when the hemostatic device is applied to the limb of the patient and the inflatable balloon is inflated, a part of the curved inner side of the more rigid part overlies the inflatable balloon and the inflatable balloon applies a compression force to a puncture site in an oblique direction with respect to a surface of the limb; and
the curved inner side part of the more rigid portion overlapping the marker as seen in a plan view from the inner side of the more rigid portion and the flexible band portion.

2. The hemostatic device according to claim 1, wherein the inflatable balloon is a first balloon, and further comprising a second balloon.

3. The hemostatic device according to claim 1, wherein the inflatable balloon is a first balloon, and further comprising a second balloon positioned between the inner side of the more rigid portion and the first balloon.

4. The hemostatic device according to claim 1, further comprising a connector that connects the inflatable balloon to the inner side of the flexible band portion.

5. The hemostatic device according to claim 1, wherein the more rigid portion overlaps a part of the flexible band portion, and further comprising a connector connected to both the inflatable balloon and the inner side of the flexible band portion to connect the inflatable balloon to the flexible band portion, the connector being connected to the inner side of the flexible band portion at a position in which the more rigid portion does not overlap a part of the flexible band portion.

6. The hemostatic device according to claim 1, wherein the curved inner side part of the more rigid portion is a first curved inner side part, the inner side of the more rigid portion comprising a second curved inner side part that is spaced from the first curved inner side part, the inner side of the more rigid portion also comprising a flat inner side part that is flat and that is positioned between the first curved inner side part and the second curved inner side part.

7. The hemostatic device according to claim 1, wherein the marker is provided on the inflatable balloon.

8. A hemostatic device to stop bleeding at a puncture site on a limb of a patient, the hemostatic device comprising:
a flexible band configured to be wrapped around at least a portion of a limb of a patient to apply the hemostatic device to the limb of the patient, the flexible band possessing opposite end portions, at least one of the end portions overlapping another portion of the flexible band when the hemostatic device is applied to the limb of the patient;
a plate held on the flexible band at a position between the two end portions of the flexible band, the plate being more rigid than the flexible band, the plate possessing an inner side that faces toward the limb of the patient when the hemostatic device is applied to the limb of the patient;
an inflatable balloon that inflates when a fluid is introduced into the inflatable balloon, the inflatable balloon being positioned to contact a surface of the patient's limb when the inflatable balloon is inflated while the hemostatic device is applied to the limb of the patient;
the inner side of the plate including a curved inner side part that is curved and a flat inner side part that is flat;
a visually viewable marker facilitates positioning the hemostatic device on the limb of the patient so that the inflatable balloon is positioned to apply a compression force to a puncture site in an oblique direction with respect to a surface of the limb;
the inflatable balloon being located at the inner side of the plate so that the inflatable balloon is between the inner side of the plate and the limb of the patient when the hemostatic device is applied to the limb of the patient;
the inflatable balloon being positioned relative to the curved inner side part of the plate such that when the hemostatic device is applied to the limb of the patient and the inflatable balloon is inflated, a part of the curved inner side of the plate overlies the inflatable balloon and the inflatable balloon applies a compression force to a puncture site in the oblique direction with respect to the surface of the limb; and
the curved inner side part of the plate overlapping the marker as seen in a plan view from the inner side of the plate and the flexible band.

9. The hemostatic device according to claim 8, wherein the inflatable balloon is a first balloon, and further comprising a second balloon.

10. The hemostatic device according to claim 8, wherein the inflatable balloon is a first balloon, and further comprising a second balloon positioned between the inner side of the more rigid portion and the first balloon.

11. The hemostatic device according to claim 8, further comprising a connector that connects the inflatable balloon to the inner side of the flexible band portion.

12. The hemostatic device according to claim 8, wherein the plate overlaps a part of the flexible band, and further comprising a connector connected to both the inflatable balloon and the inner side of the flexible band to connect the inflatable balloon to the flexible band, the connector being connected to the inner side of the flexible band at a position in which the plate does not overlap a part of the flexible band.

13. The hemostatic device according to claim 8, wherein the curved inner side part of the plate is a first curved inner side part, the inner side of the plate comprising a second curved inner side part that is spaced from the first curved inner side part, the flat inner side part being positioned between the first curved inner side part and the second curved inner side part.

14. The hemostatic device according to claim 8, further comprising a connector that connects the inflatable balloon to the inner side of the flexible band, the connector and the inflatable balloon being made of the same material, the inflatable balloon being connected to the flexible band solely by way of the connector.

15. The hemostatic device according to claim 8, wherein the marker is positioned so that in plan view the marker is centered on the inflatable balloon.

16. The hemostatic device according to claim 15, wherein the marker is provided on the inflatable balloon.

17. A hemostatic device to stop bleeding at a puncture site on a limb of a patient, the hemostatic device comprising:
a flexible band configured to be wrapped around at least a portion of a limb of a patient to apply the hemostatic device to the limb of the patient, the flexible band possessing opposite end portions spaced apart from one another in a lengthwise direction of the flexible band, at least one of the end portions overlapping another portion of the flexible band when the hemostatic device is applied to the limb of the patient;
a plate on the flexible band, the plate being more rigid than the flexible band, the plate possessing an inner side that faces toward the limb of the patient when the hemostatic device is applied to the limb of the patient;
an inflatable balloon that inflates when a fluid is introduced into the inflatable balloon, the inflatable balloon being positioned to contact a surface of the patient's limb when the inflatable balloon is inflated while the hemostatic device is applied to the limb of the patient;
the inner side of the plate including a curved inner side part;
the inflatable balloon being located at the inner side of the plate so that the inflatable balloon is between the inner side of the plate and the limb of the patient when the hemostatic device is applied to the limb of the patient;
the inflatable balloon being located on the inner side of the plate at a position deviated to a first end of the plate from a center of the plate in the lengthwise direction of the flexible band;
a marker positioned in alignment with a center of the inflatable balloon to facilitate positioning the hemostatic device when applying the hemostatic device to the limb of the patient so that when the hemostatic device is applied to the limb of the patient the marker overlies the puncture site;

the inflatable balloon being positioned relative to the curved inner side part of the plate such that when the hemostatic device is applied to the limb of the patient and the inflatable balloon is inflated, a part of the curved inner side of the plate overlies the inflatable balloon and the inflatable balloon applies a compression force to a puncture site in an oblique direction with respect to a surface of the limb; and the curved inner side part of the plate overlapping the marker as seen in a plan view from the inner side of the plate.

18. The hemostatic device according to claim 17, wherein the marker is provided on the inflatable balloon.

19. The hemostatic device according to claim 17, wherein the inner side of the plate includes a flat inner side part that is flat.

20. The hemostatic device according to claim 17, further comprising a connector that connects the inflatable balloon to the inner side of the flexible band, the connector and the inflatable balloon being made of the same material, the inflatable balloon being connected to the flexible band solely by way of the connector.

* * * * *